(12) United States Patent
Merriman et al.

(10) Patent No.: US 9,068,221 B2
(45) Date of Patent: Jun. 30, 2015

(54) METHOD OF ANALYSIS OF GENETIC MARKERS

(75) Inventors: Barry Merriman, Encinitas, CA (US); Paul Mola, San Diego, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/370,177

(22) Filed: Feb. 9, 2012

(65) Prior Publication Data
US 2012/0214256 A1 Aug. 23, 2012

Related U.S. Application Data

(60) Provisional application No. 61/441,210, filed on Feb. 9, 2011.

(51) Int. Cl.
*C12Q 1/68* (2006.01)

(52) U.S. Cl.
CPC .......... *C12Q 1/6827* (2013.01); *C12Q 1/6816* (2013.01)

(58) Field of Classification Search
None
See application file for complete search history.

(56) References Cited

U.S. PATENT DOCUMENTS

| 6,936,433 B2 * | 8/2005 | Akeson et al. ................. 435/23 |
| 2011/0168562 A1 * | 7/2011 | Nuckolls et al. ............. 204/600 |

FOREIGN PATENT DOCUMENTS

WO    2007117832    10/2007

OTHER PUBLICATIONS

Wiggin, "Genotyping by Nanopore Force Spectroscopy: Method Development and Evaluation for Clinical Diagnostics," University of British Columbia, Vancouver, Nov. 2009 (thesis).*
PCT/US2012/024544 International Search Report and Written Opinion mailed Aug. 31, 2012.
Choi, Jong Y. et al., "An integrated microdevice for high-performance short tandem repeat genotyping", *Biotechnology Journal*, vol. 4, No. 11, 2009, 1530-1541.
Luo, Kaifu et al., "Dynamics of DNA translocation through an attractive nanopore", *Physical Review E*; vol. 78, No. 6, 2008, 1-7.
Nakane, Jonathan et al., "A Nanosensor for Transmembrane Capture and Identification of Single Nucleic Acid Molecules", *Biophysical Journal*, vol. 87, 2004, 615-621.
Wanunu, Meni et al., "DNA Translocation Governed by Interactions with Solid-State Nanopores", *Biophysical Journal*, vol. 95, No. 10, 2008, 4716-4725.
Wiggin, Matthew J., "Genotyping by Nanopore Force Spectroscopy: Method Development and Evaluation for Clinical Diagnostics", *Thesis for Doctor of Philosophy*; XP55035893, Jan. 1, 2009, 1-193.

* cited by examiner

*Primary Examiner* — Bradley L Sisson

(57) ABSTRACT

A method of analyzing genetic markers includes binding a set of probes to a segment of single stranded nucleic acids. The segment of single stranded nucleic acids includes a repeat region formed of at least two of a repeat unit. The repeat unit can include at least two nucleic acids. The set of probes includes a first probe complementary to the repeat unit. The method can further include directing the segment through a nanopore device and measuring a signal through the nanopore device. The signal can be indicative of the number of repeat units.

10 Claims, 6 Drawing Sheets

N = 11 [GATA] REPEATS     (SEQ ID NO. 5)

HUNTINGTON'S DISEASE: CAG REPEAT IN HTT GENE

| REPEAT COUNT | CLASSIFICATION | DISEASE STATUS |
|---|---|---|
| <27 | NORMAL | UNAFFECTED |
| 27-35 | INTERMEDIATE | UNAFFECTED |
| 36-39 | VARIABLE PENETRANCE | +/- AFFECTED |
| >39 | FULL PENETRANCE | AFFECTED |
| >60 | JUVENILE ONSET | AFFECTED |

METHOD OF ANALYSIS OF GENETIC MARKERS

CROSS-REFERENCE TO RELATED APPLICATION(S)

This application claims benefit of U.S. Provisional Application No. 61/441,210, filed Feb. 9, 2011, which is incorporated herein by reference in its entirety.

REFERENCE TO BIOLOGICAL SEQUENCE DISCLOSURE

This application contains nucleotide sequence and/or amino acid sequence disclosure in computer readable form (LT00445_ST25.txt, Created May 1, 2012, size 2 KB) and a written sequence listing, the entire contents of both of which are expressly incorporated by reference in their entirety as though fully set forth herein.

FIELD OF THE DISCLOSURE

This disclosure, in general, relates to methods of analyzing or detecting genetic markers, for example, using nanopore devices.

BACKGROUND

There has been increasing interest in using genetic markers for human identification (HID). Such identification is particularly useful in forensic applications, paternity testing, and inherited disease analysis. However, conventional methods, such as gel electrophoresis sizing, are time consuming and labor intensive.

As such, an improved method of detecting or analyzing genetic markers would be desirable.

SUMMARY

In a first aspect, a method for analyzing genetic markers includes binding a set of probes to a segment of single stranded nucleic acids. The segment of single stranded nucleic acids includes a repeat region formed of at least two of a repeat unit. In an embodiment, the repeat unit includes at least two nucleic acids. The set of probes includes a first probe complementary to the repeat unit. The method may further include directing the segment through a nanopore device, stripping the bound probes of the set of probes from the segment, and measuring a signal through the nanopore device. Among others, the signal is indicative of the number of repeat units.

In a second aspect, a method of determining genotype includes receiving a current trace including current spikes associated with translation of a strand of nucleic acids through a nanopore and stripping probes from the strand, the probes associated with a repeat unit of the strand of nucleic acids. The method further includes determining a genotype based on one or more characteristics of the current spikes.

In a third aspect, a method of determining genotype includes mixing a set of binding probes with a set of single stranded nucleic acid segments. The set of single stranded nucleic acid segments may include a first segment associated with a first gene and a second segment associated with a second gene. The first segment includes a first repeating section of first repeating units. The second segment includes a second repeating section of second repeating units. The set of binding probes includes a first probe complementary to the first repeating units, a second probe uniquely associated with the first segment and complementary to a region of the first segment, and a third probe complementary to the second repeating units. The method further includes directing the segments through a nanopore device, stripping the probes of the set of probes from the segments, and measuring a current through the nanopore device to provide a current trace. The current trace includes current spikes indicative of stripping the first probe and the second probe.

In a fourth aspect, a kit includes a probe having a sequence complementary to a repeat unit of a repeat region of a segment of single stranded nucleic acids associated with an allele.

In a fifth aspect, a kit includes a first probe having a sequence complementary to a common region of a segment of single stranded nucleic acids associated with a gene and a second probe having a sequence complementary to a variant region of the segment of single stranded nucleic acids associated with the gene.

In a sixth aspect, a method of determining genotype includes receiving a current trace including current spikes associated with translation of a strand of nucleic acids through a nanopore. The strand includes double stranded regions associated with hybridized probes. The probes are associated with a tandem repeat segment of the strand of nucleic acids. The method can further include determining a genotype based on a characteristic of the current spikes.

The aforementioned aspects of the disclosure are exemplary and non-limiting.

BRIEF DESCRIPTION OF THE DRAWINGS

The disclosure will be discussed in reference with the following exemplary and non-limiting drawings in which liked elements may be represented with like numbers.

DETAILED DESCRIPTION

In an embodiment, a method for detecting or analyzing markers includes using a nanopore or a current (e.g., ion current) sensor to determine, for example, genotypes of microsatellite markers. Such a method can be used to replace current gel size separation methods conventionally used for typing such markers. An example of the method includes starting with a single stranded DNA molecule containing a microsatellite repeat tract or segment, binding probes corresponding to a repeat unit of the repeat tract, populating the tract sequentially and contiguously, and serially stripping off the bound probes as the strand passes through a nanopore. The method can further include counting the resulting spikes in the ion current through the pore to determine the repeat count, which can be used to type the microsatellite marker. By averaging repeated measurements, either on the same strand trapped in the pore or on independent duplicate strands, the accuracy of the procedure can be improved to a high level of confidence.

To type other forms of markers, such a method can be extended to binding probes designed to bind sequentially along the length of a strand fragment, some of which are allele-specific and some of which are invariant across alleles of interest. Some of the probes may bind with different affinity depending on the allele. As the strand passes through the nanopore and the probes are sequentially stripped away, the measured current can include a spike pattern. The number of current spikes can correspond to the number of probes removed, or the time intervals between current spikes can correspond to differential binding affinity of the probes, providing a measurement that can be use to determine which allele has passed through the nanopore.

Microsatellite genetic markers are DNA sequence elements in the genome of a particular species, in which a simple sequence unit (repeat unit) of a length k (e.g., k=3) repeats N times, and in which N is variable, or polymorphic, across individuals of that species. The microsatellite genetic markers can thus be used as a traceable marker to distinguish the DNA from different individuals within the species. Microsatellite markers are also interchangeably referred to as Short Tandem Repeat (STR) or Variable Nucleotide Tandem Repeat (VNTR) markers.

For example, the sequence S=GATGATGATGAT (SEQ ID NO. 1) can be a microsatellite with repeat unit [GAT], which is a k=3 mer, and a repeat count of N=4. In other examples, the repeat unit can include at least two nucleic acids, such as at least three nucleic acids, at least four nucleic acids, at least five nucleic acids, or even at least six nucleic acids. Typically, k is in the range of 2 to 5, such as in a range of 3 to 5. The microsatellite can include at least four repeat units (i.e., N≥4), such as at least six repeat units, or at least 10 repeat units. For example, N can be in the range of 10 to 30.

Figure 1:
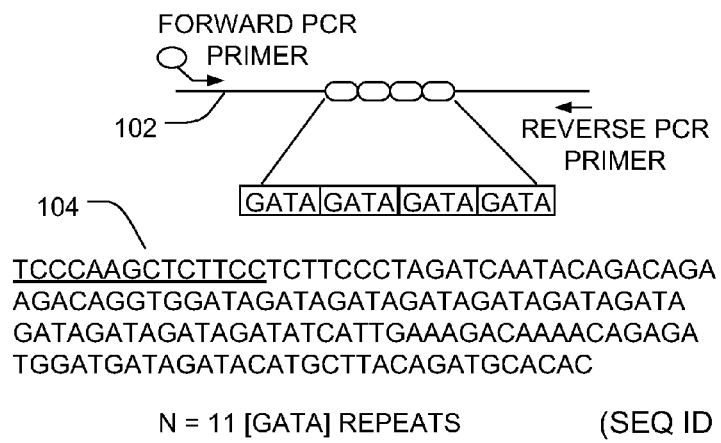
FIG. 1 illustrates a microsatellite or STR marker.
Figure 1:
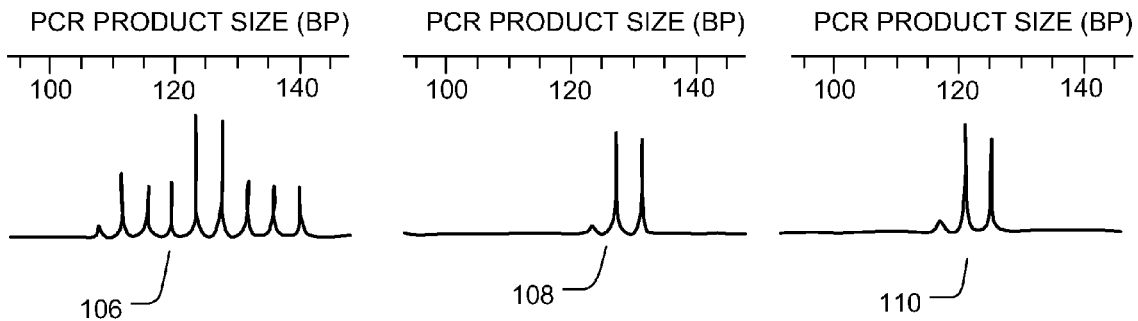

In a particular example, FIG. 1 includes an illustration of a microsatellite or STR marker. In the upper left of FIG. 1 illustrates how polymerase chain reaction (PCR) can be used to amplify the fragment 102 of interest. The lower left of FIG. 1 illustrates a conventional sequence 104 for a [GATA] repeat, with N=11 repeat units of size k=4. The right panel of FIG. 1 illustrates the genotypes of two individuals (108, 110), relative to a ladder 106 of the possible fragment sizes, as can be used in a standard gel sizing analysis.

A collection of several such markers in the genome can be used as a "DNA fingerprint" to reliably identify or distinguish individuals, for example, for criminal or forensic applications, or can be used to trace inheritance of portions of the genome that are passed from parent to child, for example, in the context of paternity testing or in performing genetic linkage studies that correlate inherited disease with inherited DNA fragments to isolate the causative genetic variants.

Figures 3, 4:
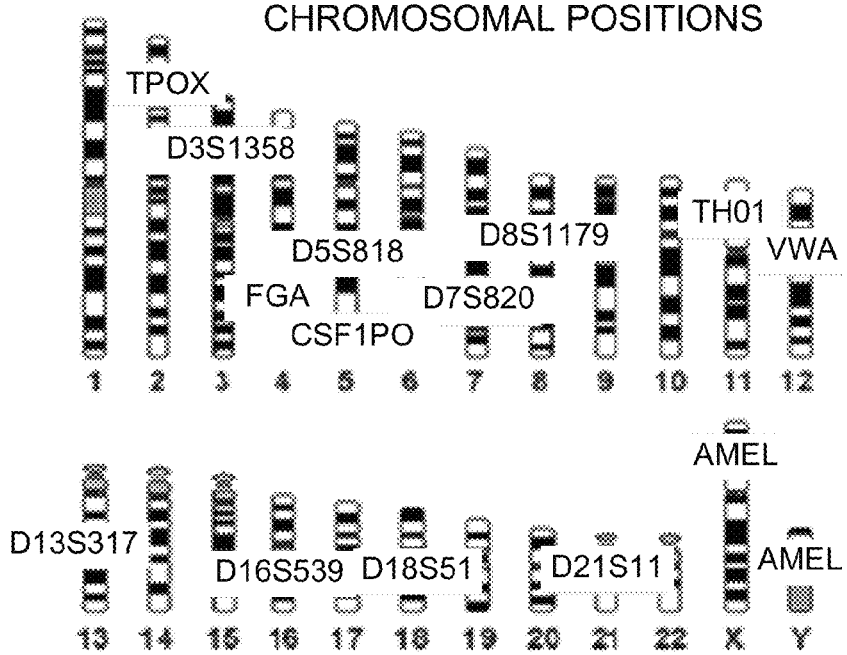
FIG. 3 illustrates an example of a disease caused by triplet repeats.
FIG. 4 illustrates an exemplary genome location of the 13 CODIS markers used by the Federal Bureau of Investigation for human identification.

There are also cases of specific microsatellite repeats that appear within genes, in which the number of repeat units has functional implications and may be the difference between a disease or non-disease state. In particular, such functional implications occur in triplet repeat expansion disorders, such as Huntington's disease, where k=3 and the repeat units code for amino acids. An excessive number N of repeat units produces a long, dysfunctional protein resulting in disease. As illustrated in FIG. 3, the repeat causing Huntington's disease occurs within the coding part of the HTT gene. The number of repeat units alters the resulting protein. The repeat length is related to disease severity, as indicated, with lengths <27 being normal.

For a given microsatellite marker, the number of repeat units that occur in an individual is referred to as their genotype at that marker. In the case of diploid organisms, each marker in the autosome occurs as two alleles, and the genotype is a pair of numbers (N1, N2) that characterize the repeat numbers of the two alleles. Generally, the genotype numbers are the number of repeat units, but in current practice, the length of a PCR amplicon including the marker is used as a correlate. The two numbers refer to length of the PCR product resulting from that individual, (L1, L2), which is measured from the banding pattern that results when the amplicons are run on a electrophoresis size separation gel, in either slab or capillary format.

Typically, microsatellite markers have repeat unit lengths of at least two nucleic acids, such as at least three nucleic acids, at least four nucleic acids, at least five nucleic acids, or even at least six nucleic acids. Typically, k is in the range of 2 to 6, such as in a range of 2 to 5 or a range of 2 to 6. The microsatellite can include at least four repeat units (i.e., N≥4), such as at least six repeat units, or at least 10 repeat units. The number (N) of repeat units typically varies between 5 and 30, such as between 10 and 30, although for each given microsatellite, typically only 4 to 10 different repeat states (N values) are observed in the population.

Figure 2:
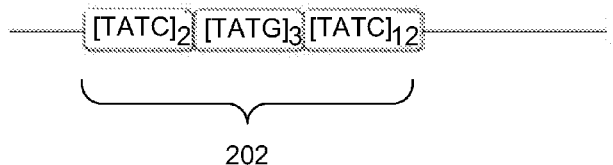
FIG. 2 illustrates an example of a microsatellite with an imperfect repeat structure.

The repeat unit may not be exactly repeated, rather there may be minor mutations to the repeat structure that have accrued over the course of evolution of the species in question. For example, a k=3, N=4 repeat that corresponds to GAAGAAGAAGAAGAA (SEQ ID NO. 2) may occur in the species as GAAGAAGATGAAGAA (SEQ ID NO. 3), wherein one of the A bases has mutated to a T in an ancient mutational event now fixed in the species. See FIG. 2 for a further example. Such imperfect repeats are still generally considered microsatellites and are of the same utility as polymorphic markers. FIG. 2 includes an illustration of an example of a microsatellite 202 with an imperfect repeat structure. The consensus repeat unit [TATC] co-occurs with units that are [TGTC].

Figure 5:
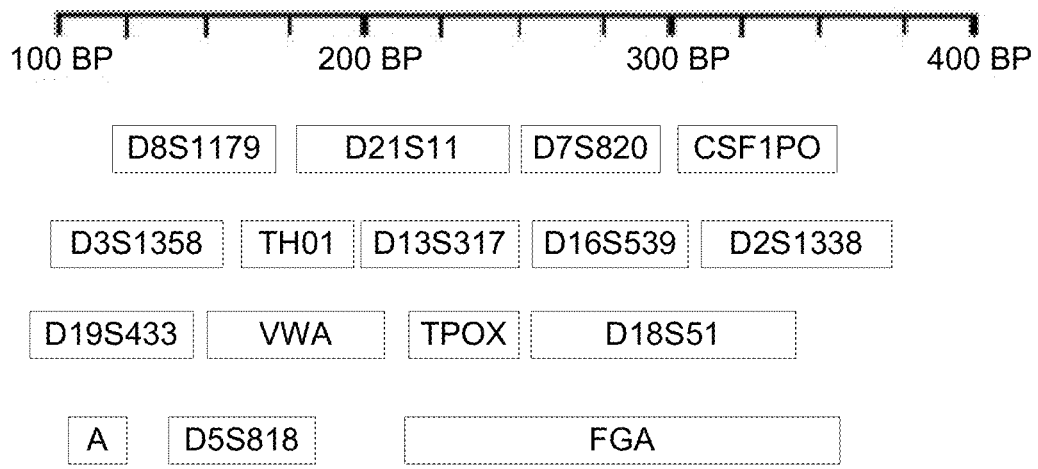
FIG. 5 illustrates size ranges of PCR products used to type the CODIS markers.

An example of a panel of markers widely used for Human Identification (HID) purposes is the Combined DNA Index System (CODIS) (see FIG. 4 and FIG. 5), which is the basis of the DNA fingerprint database used by the FBI in the United States. As illustrated in FIG. 4, CODIS consists of 13 different autosomal microsatellite markers with tetra nucleotide repeats (unit length k=4) and with N in the ranges of 10-30. FIG. 5 illustrates size ranges of PCR products used to type the CODIS markers. The fragments range from 100 bases to 400 bases in length. Each row indicates a different dye used to multiplex the gel sizing.

In addition, the CODIS system uses the AMEL marker to determine sex, which is a marker with alleles on the X and Y chromosomes. Such a marker is not a microsatellite, but instead differs by a 6-letter deletion on X, which allows distinction between the form on the X and Y-chromosomes, and thus allows distinction between XY (male) and XX (female) types. Even though AMEL is not a microsatellite, it can be typed using a form of the nanopore-based technique described here.

Other closely related sets are used for standardized HID in various other countries or regions, for example:

U.S. Core Loci (CODIS): CSF1PO, FGA, TH01, TPOX, VWA, D3S1358, D5S818, D7S820, D8S1179, D13S317, D16S539, D18S51, D21S11, AMEL Extended European Standard Set (ESS): FGA, TH01, VWA, D1S1656, D2S441, D3S1358, D8S1179, D10S1248, D12S391, D18S51, D21S11, D22S1045 Additional European Loci: D2S1338, D16S539, D19S433, SE33, AMEL UK Core Loci: FGA, TH01, VWA, D2S1338, D3S1358, D8S1179, D16S539, D18S51, D19S433, D21S11, AMEL German Core Loci: FGA, TH01, SE33, VWA, D3S1358, D8S1179, D18S51, D21S11, AMEL Interpol Standard Set of Loci: FGA, TH01, VWA, D3S1358, D8S1179, D18S51, D21S11; Optional: AMEL A nanopore sensor is a small, nanometer-scale, channel, hole or "pore" passing through a physical barrier otherwise impermeable to ions. In particular embodiments, when the pore is in contact with an ionic solution and placed under a suitable applied voltage, a measurable ion current flows. When the pore or channel is partially obstructed by the presence of another molecule, the current is altered. In this way, the sensor can be used to make measurements on molecules that block or pass through the pore, particularly those that carry a charge in solution and are thus driven into or through the pore by the applied voltage. In another embodiment, the presence of particular molecules, such as nucleic acids of a nucleic acid strand cause a change in the nanopore, such as a chance in conductance within a semiconductor region or a change in conductance through the fluid within the pore, that results in a signal characteristic of the nucleic acid.

In particular, in the context of measuring DNA, the DNA strand may be induced to pass through the pore, and there can be differential current signals for single stranded DNA, double stranded DNA, for different adducts bound to such DNA, and even due to the base composition of the DNA itself. The nanopore can be a porin protein, such as Alpha Hemolysin (aHL), or MspA, either in their native or mutant forms, embedded in a lipid bilayer (See FIG. 6), or can be a fabricated hole created in a solid state membrane using techniques from lithography and semiconductor manufacturing, such as e-beam lithography, photolithography, or chemical vapor deposition. In an example, the nanopore can be structured as a passive circuit including two electrodes. In another example, the nanopore can be structured as an active circuit, such as an FET device including a source, drain, and gate material.

Figure 6:
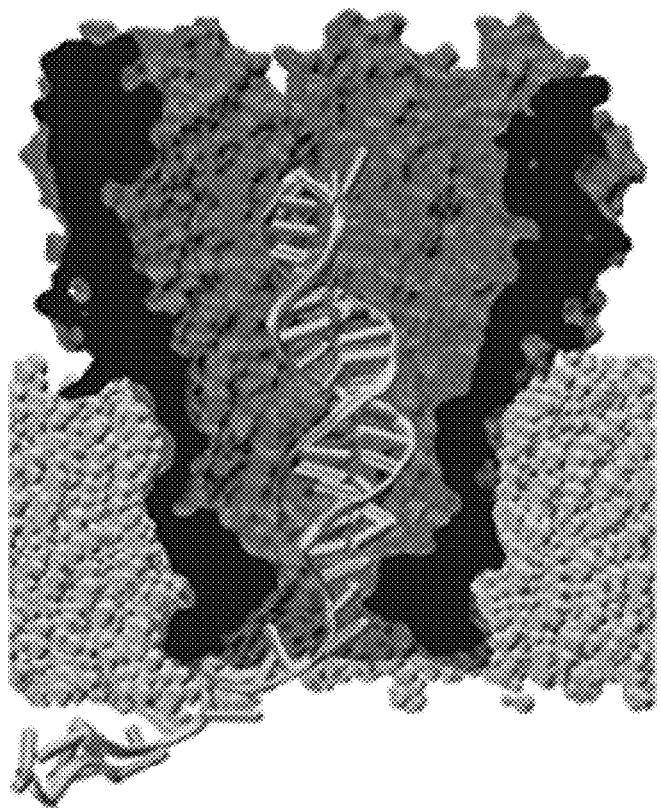
FIG. 6 is a cross sectional view of an exemplary protein nanopore (MspA) containing a strand of single stranded DNA.

FIG. 6 includes an illustration of a cross-sectional view of a protein nanopore (MspA) containing a strand of single stranded DNA, whose motion through the channel has been blocked by the binding of a complementary DNA binding probe (double stranded region). The ionic current through the pore is reduced by the double strand.

The microsatellite marker to be studied can be suitably isolated in single stranded form from the genomic source DNA. In particular, the isolated single strand can be prepared using PCR amplification. Such DNA can be produced in single stranded form by denaturing, by asymmetric PCR, or by the use of biotinylated primers to extract a single strand. In an example, the single stranded DNA can be exposed to a solution containing k-mer DNA binding probes complementary to the k-mer unit of the microsatellite repeat unit, which can bind to the sites along the strand. A nanopore is utilized such that single stranded DNA can pass through the constriction under a suitable driving force. DNA bound with the binding probe is too large to pass through the nanopore and is physically blocked from passing through the pore. The driving force and other environmental factors are chosen such that the blockage from the short binding probe persists for a short period before being stripped off. The resulting pore channel current versus time behavior includes a low current during the blockage phase and can include a spike of current when the stripping event occurs and the strand slips forward through the pore to the position of the next binding probe, such as at the next repeat unit of the microsatellite sequence. See, for example, FIG. 7. In this way, a current spike can be produced as each repeat unit has its complementary probe stripped away, and the DNA advances through the pore. As a result, the number of repeat units can be measured by counting the current spikes in the current versus time trace.

Figure 7:
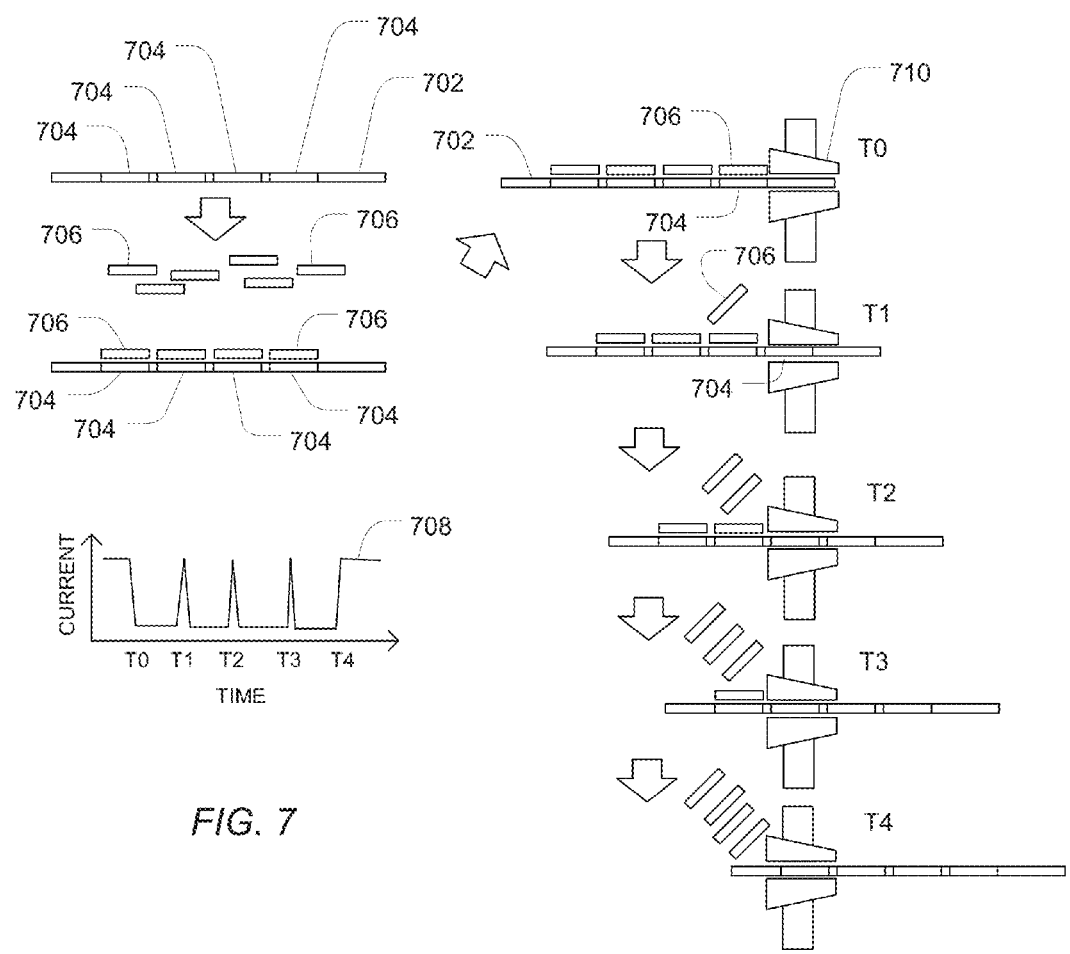
FIG. 7 illustrates an exemplary fragment containing microsatellite repeat units and probes complementary to the units.

As illustrated in FIG. 7, a fragment or segment containing a microsatellite repeat 704 is bound to complementary probes 706. As the fragment 702 passes through the pore 710, the DNA strand motion pauses, and the probes are stripped away. Alternatively, the double stranded region formed by the probes can pass through the pore. In either case, the movement of the fragment 702 and probes produces a signal or current trace 708. The resulting current trace 708 for the ion current through the pore includes upward current spikes each time a probe is stripped off (e.g., T1, T2, T3), spiking up to the ambient level for single stranded DNA in the pore (e.g., before T0, after T4).

It should be noted that the k-mer binding probes may have targets on the fragment outside of the primary repeat tract, since, for example, the same k-mer can appear in the adjacent sequence context, near but not as part of the repeat tract. In such a case, additional spikes can result, and the number of spikes may not equal the number of units. Such a difference does not alter the value of the measurement for marker typing, since the current spikes represent a polymorphic measurement that distinguishes the different underlying genotypes.

Thus, through this process of binding probes to repeat units, stripping the probes as the probes pass through the pore, and counting the resulting current spikes, the microsatellite marker repeat length of the specific DNA fragment is characterized. In the course of processing many DNA fragments, either serially through the same pore or in parallel through multiple pores, the alleles of the microsatellite can be observed, and the genotype thus determined.

It is desirable to extend the microsatellite typing technique to other forms of polymorphic genetic markers. For example, in the CODIS marker panel for human identification, while the primary 13 identity-determining markers are microsatellites, the additional marker used to determine sex, AMEL (Amelogenin), is not in the microsatellite form, and it would be desirable when typing the CODIS panel to be able to assess AMEL by a similar procedure. AMEL is a DNA sequence variant in which the sequence occurring on the X chromosome, AMELX, has a 6-base pair deletion relative to the version that occurs on the homologous locus on the Y chromosome, AMELY, such that the PCR products produced are 106 and 112 bases long, respectively.

The present method can be utilized to type the AMEL marker. Instead of counting binding probes that attach to repeat unites, a pool of binding probes includes N number of probes that are targeted to attach to the common parts of the sequence fragment, plus M number of allele-specific probes that attach to a particular variant form, and not others. Using such a pool of binding probes in the present method results in a number of current spikes in which the fragments have N or N+M spikes, depending on whether they bind the N common probes or both the N common probes and the M additional allele specific probes. See FIG. 8. A type of N is thus "not the variant allele" and a type of N+M is "the variant allele."

Figure 8:
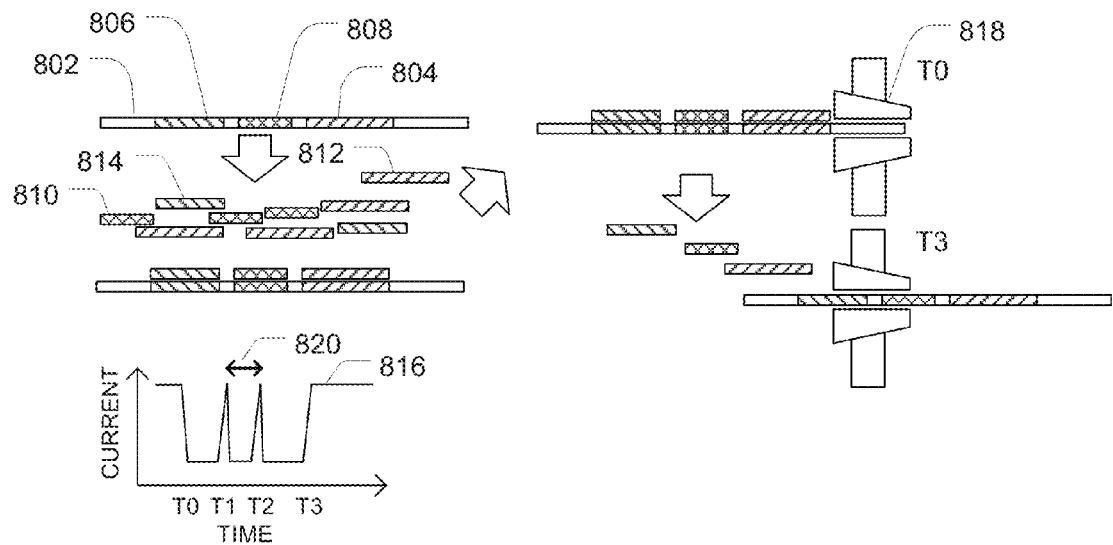
FIG. 8 illustrates an exemplary method for typing markers.
Figure 8:
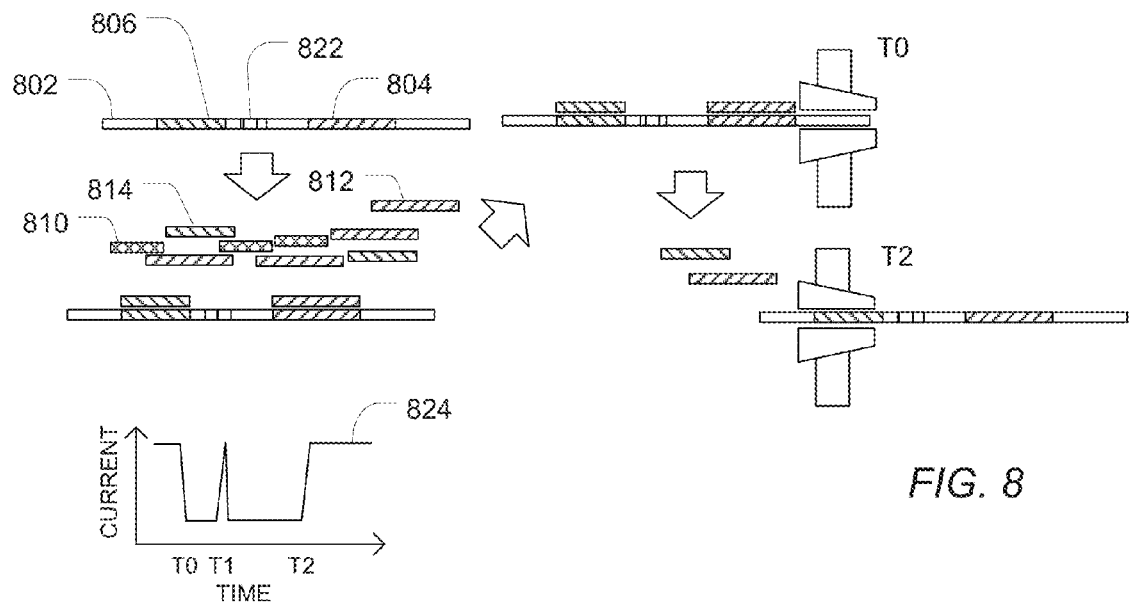

As illustrated in FIG. 8, segments 804 or 806 represent sequences common to the alleles. A sequence segment 808 on the variant allele differs from the reference. Complementary binding probes are indicated by striped segments 812, 810, or 814. The binding probes are stripped, resulting in the pattern of current spikes 818 illustrated in the upper half. Alternatively, the probes can pass through the nanopore 818 providing a trace including a pattern associated with passing a series of double and single stranded regions. The spacing 820 between the two peaks is short, indicating a case where the probe 814 does not bind tightly and is stripped more rapidly than the others. Short residence time can be an additional indicator of the allele. In the lower half of FIG. 8 is illustrated a case when the non-variant allele 822 is present. The non-variant allele 822 has no specific binding probe and results in the single spike pattern 824 illustrated in the lower half of FIG. 8. Thus, the difference in spike number distinguishes the variant allele from others which have no binding probe.

Similar to the case of microsatellites, if there are more than two variant alleles that occur in the population, it may be possible, depending on the precise form of the sequence variant, to arrange a collection of binding probes such that the number of spikes observed distinguishes the different alleles, so that multiple alleles can be simultaneously typed by the N, N+1, N+2, N+M possible spike counts, rather than a simple binary "has/does not have" allele type.

In a further example, the allele-specific binding probes can have binding energies that are different, and thus the time interval between spikes that represent the stripping of such a probe and the next probe, can distinguish the different allele types.

Figure 9:
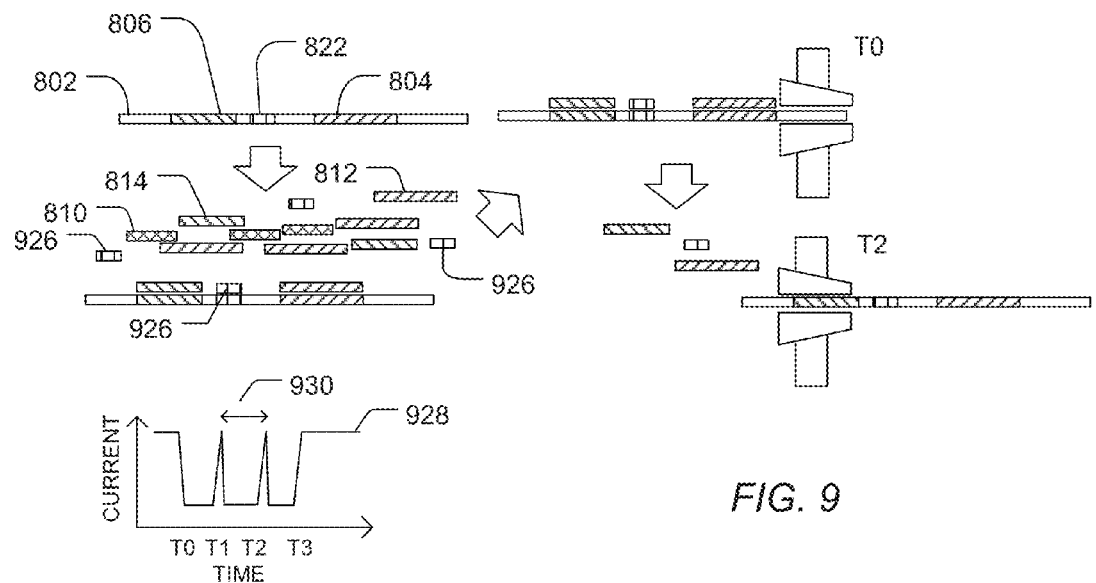
FIG. 9 illustrates an exemplary method for detecting multiple alleles using differences in stripping time to indicate the allele.

As illustrated in FIG. 9, detecting multiple alleles can be performed by using the difference in stripping time to indicate the allele. In this case, a binding probe 926 binds its allele 822 tighter than the another allele indicated in FIG. 8, resulting in a longer residence time 930, even though the number of spikes of the trace 928 is the same as for the variant allele in FIG. 8. Thus, the residence time between spikes can be used to distinguish alleles.

In a further example, the period between the first probe and the last probe can be used to distinguish alleles. Such a period can be used to confirm or validate other measurements, such as the number of spikes or the period between spikes, or can be used as a stand-alone measure for distinguishing alleles when the spikes are closely packed or difficult to distinguish.

Even for microsatellites lacking mutations in the repeat units, there may be cases where it is advantageous to make a probe different than the fundamental repeat unit. In the case of dinucleotide repeats (such as a [GA] repeat GAGAGAGA ... ), it may be impractical to make a GA binding probe, due to the low binding energies of such short probes. In such a case where the fundamental repeat unit does not result in a practical probe, the probe can be targeted at a larger portion of the repeat pattern, such as a two-unit repeat, GAGA, a three-unit repeat, or another repeating element of the pattern such as the GAG triplet that appear separated by A, (GAG-A-GAG-A ... ). While such larger footprint probes may not populate the possible [GA] repeat patterns, they may result in different current spike numbers, at least on average, which are sufficient to differentiate alleles that are present.

In an example, the binding probe is the complement of the k-mer repeat unit of the microsatellite. However, it is possible to modulate the hybridization binding energy of such probes by a variety of techniques, such as using peptide nucleic acid (PNA) or locked nucleic acid (LNA) bases instead of standard nucleic acids. Such an approach can be used to tune the binding energy of the probe or probes to match target experimental conditions. Also, it may be desirable to add additional chemical groups to the probes to make them larger or otherwise more reactive with the pore so that, for example, the stripping process can have an additional dimension of control. For example, additions that increase size of the probe can be used with pores with larger channels or pores that have more pore-to-pore variability in channel size, which in turn may permit using pores that are easier to manufacture, such as different protein families or solid state, non-biological pores.

In various techniques for testing microsatellites, noise can occur in two forms: "noise" in the repeat sequence of the microsatellite and noise in the measurement process. Regarding sequence noise, a microsatellite may not have a repeat structure without mutation, but instead, may have some k-mer units that are mutated. Such mutant forms may be fixed into all or part of the current population, depending upon age and population history. Such mutation can be considered as a form of noise that degrades the measurement process outlined above. Specifically, such mutated repeat units may not bind a probe properly, and thus may not register a spike, resulting in an error in count of the units of the microsatellite. Such an issue can be dealt with in two ways so that the marker typing achieves a useful polymorphic measurement that permits classification of the underlying genotypes. In an approach, in addition to the binding probes for the dominant k-mer repeat units, probes for the minority forms can be added as well. For example, if the mutated form is the [GAA] repeat GAAGAAGATGAAGAA (SEQ ID NO. 3), in addition to a probe binding GAA, a probe that binds GAT can be added to bind the mutated unit. Thus, there can be the desired set of spikes, one per unit.

Alternatively, the repeat unit sequence differences can be ignored, as long as the observed spikes provide a polymorphic measure that distinguishes the alleles. For example, if the variants to distinguish are N=5 (GAAGAAGATGAAGAA (SEQ ID NO. 3)), N=4 (GAAGAAGATGAA (SEQ ID NO. 4)), N=3 (GAAGAAGAT) and if no probe were to bind to GAT, there would be 4, 3, and 2 current spikes, respectively, which adequately distinguishes the alleles, even though it may not be considered the proper repeat count.

Regarding measurement noise, another form of noise is the measurement noise that comes from the stochastic nature of single molecule measurements. Because binding probe attachment, DNA motion through the pore, and ionic current through the pore are all subject to random fluctuations, such as thermal fluctuations, it is possible that repeat units could be missed (e.g., no binding attached probe, thus no current spike) or double counted (e.g., DNA undergoes a reverse motion, then resumes, so same unit counts twice).

A method of overcoming such noise is to repeat the measurement and suitably average the results, for example, averaging the individual spike counts. Such averaging can be accomplished by averaging the results of independent measurements done on different PCR product fragments representing the same allele, which can be processed either serially through a single pore or in parallel at other pores exposed to the same DNA source material.

An alternative way to average is to trap a fragment in the pore and use a "flossing" technique of running the DNA back and forth through the pore repeatedly to re-measure the same fragment until sufficient accuracy is achieved. Various techniques can be used to secure the fragment, as long as the binding probes can rebind between each measurement attempt. Such is the case if the probes are generally present in solution on one or both sides of the pore. Specific flossing methods include creating obstructions or caps at both ends of the DNA molecule, such as using hairpin sequence structures or attached streptavadin molecules, which lock the DNA in the pore and prevent the ends from exiting, combined with procedures to first cap one end, thread the pore, then cap the other. A reversible driving force, such as a voltage, can be used to control the forward and reverse motion of the DNA in the pore.

Figure 10:
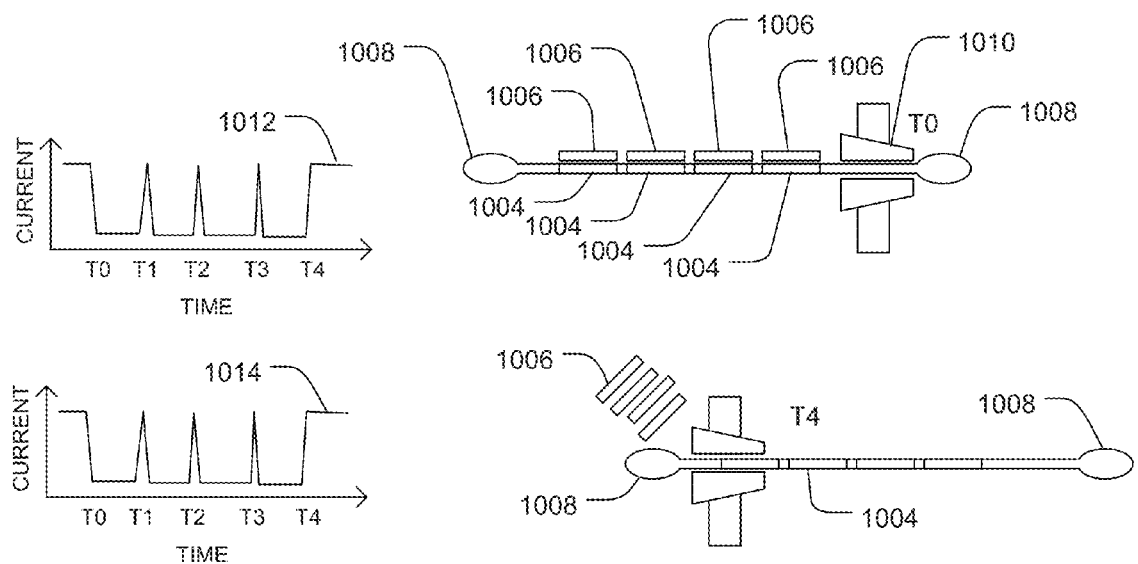
FIG. 10 illustrates flossing for repeating the measurement to improve accuracy.

As illustrated in FIG. 10, flossing can be used to repeat the measurement to improve accuracy. Once established, blocking structures 1008 on the ends keep the strand 1002 trapped in the pore. By moving the strand 1002 back and forth and allowing it to rebind the probes 1006, multiple traces (1012, 1014) can be obtained for the same fragment, and such traces can be suitably averaged to obtain an accurate consensus trace, or count of peaks or time between peaks. Such a flossing method is particularly useful when averaging the period between the first and last spikes (T4-T0), providing an alternative method for distinguishing alleles.

While the methods have been described in relation to a single allele, multiplex testing of markers can be achieved using the above framework. For example, in the context of testing the 13 CODIS markers, the 13 markers can be typed separately, either in different sensor-containing assay chambers at the same time, or delivered serially to a single sensor chamber, with suitable washing in between, or any combination thereof. Alternatively, it may be desirable to multiplex multiple markers into a single sensor chamber, to reduce the number of sensor chambers utilized. Such multiplexing can be achieved by using the general binding probe technique to barcode the different sequence fragments with distinguishable barcodes, in the form of a pattern of some number of current spikes and spike spacings that allows the different resulting spike patterns to be assigned to the respective different markers under consideration. Probes specific to non-repeating sections of the segment associated with a marker can be applied in a manner to provide a pattern of spikes that identify the segment relative to other multiplexed segments. Alternatively, the probes may be manipulated to provide current spikes with a distinct characteristic for alleles within the multiplexed sample. As such, a measurement of a particular allele can be differentiated from measurements associated with other alleles.

In a particular embodiment, a method for distinguishing the alleles of a genetic marker includes making DNA fragments single stranded, binding to a pool of DNA binding probes that are specific for non-overlapping sites along the marker, some of which are allele specific in either their binding or in their tightness of binding, and inducing the DNA fragment to move through a nanopore sensor in such a way that the binding probes transiently block motion through the pore and reduce current through the pore. The method further includes stripping away the binding probes as the strand further moves through the pore under action of the driving force in such a way that the resulting current trace has discernible spikes and such that the number of spikes or spacing between spikes provides a classification of the alleles.

In an example of the embodiment, the alleles are those of a microsatellite marker with a k-mer repeat structure, the binding probes are DNA k-mers complementary to the repeat unit on the DNA strand to be interrogated, and the number of current spikes is uses to characterize the allele. Further, the repeat sequence of the microsatellite may include mutations, but the k-mers are complementary to the consensus k-mer unit. In another example, the microsatellite includes mutations and a pool of different k-mers complementary to the different mutated forms of the consensus k-mer is used.

In a further example of the embodiment, the variant is an insertion or deletion of a sequence relative to a reference form and the set of probes include sequence probes that bind on one or both sides of the variable site on the alleles and include a probe or probes that bind (under the proper reaction conditions) only to the variant form, but not to the reference form of the allele, or vice versa. The number of current spikes characterizes the allele as having or not having the variant.

In an additional example of the embodiment, the variant is an insertion or deletion of sequence, and the set of probes includes sequence probes that bind on one or both sides of the variable site and include probes for both the reference and variant allele(s) which have different characteristic residence time in the nanopore before the stripping event occurs. The number of current spikes as well as the time between spikes is used to classify the allele. In an example, the variant is a single nucleotide variant, but otherwise treated by the same strategy.

In another example of the embodiment and related examples, the pore is a protein pore, of native type or mutated, or a non-biological pore, and the DNA motion can be caused by applied voltages, chemical changes, temperature changes, the use of optical or magnetic tweezers, or the use of a molecular motor or enzyme to draw the DNA through the pore.

In a further example of the embodiment and related examples, the binding probes are DNA probes complementary to the target sequences, or are modified by the presence of LNA, PNA or other modified bases to alter binding affinities. The binding probe can be further altered by the addition of a chemical group that increases the size or reactivity of the probe with the pore to achieve the desirable stripping effect for the pore.

In an additional example of the embodiment and related examples, a measurement is made more accurate through the use of averaging of repeat measurements, either across independent measurements of copies of the same fragment or through repeated measurements on the same fragment achieved by a flossing procedure to repeatedly move the same fragment back and forth through the pore.

In another example of the embodiment and related examples, the method can be applied to typing the markers from the CODIS panel used for human identification (HID) in the United States, and for similar standard panels that used for HID in Europe, Asia, and other countries or regions.

In a further example of the embodiment and related examples, the method can be applied to typing microsatellite markers from linkage analysis panels, such as the Marshfield panel of markers.

In an additional example of the embodiment and related examples, the binding probes bind some other repeating structure within the repeat tract, other than the fundamental repeat unit. For example, in the case of a di-nucleotide repeat, [AB], the binding probes target [ABAB], [BABA], [ABA], or [BAB].

In an additional embodiment, the methods of proceeding examples and embodiments are used for multiplex testing of markers. An additional set of binding probes provides a distinguishable barcode spike pattern (number or spacing) that allows measured types to be assigned to the respective markers, based on the total observed spike pattern.

In a first aspect, a method of analyzing genetic markers includes binding a set of probes to a segment of single stranded nucleic acids. The segment of single stranded nucleic acids includes a repeat region formed of at least two of a repeat unit. The repeat unit includes at least two nucleic acids. The set of probes includes a first probe complementary to the repeat unit. The method further includes directing the segment through a nanopore device, and measuring a signal through the nanopore device. The signal is indicative of the number of repeat units. For example, the method can include stripping the bound probes of the set of probes from the segment. Alternative, the signal can be indicative of double stranded regions associated with the bound probes passing through the nanopore device.

In an example of the first aspect, the repeat unit includes at least 3 nucleic acids. For example, the repeat unit includes at least 4 nucleic acids, such as at least 5 nucleic acids, at least 6 nucleic acids. In an example, the repeat unit includes a number of nucleic acids in a range of 3 to 5.

In another example of the first aspect and the above examples, the set of probes includes a second probe complementary to a mutation of the repeat unit.

In an additional example of the first aspect and the above examples, the first probe complementary to the repeat unit is complementary to at least two consecutive repeat units. For example, the first probe is complementary to at least three consecutive repeat units.

In a further example of the first aspect and the above examples, the first probe complementary to the repeat unit is complementary to a subset of consecutive nucleic acids in at least two adjacent repeat units.

In another example of the first aspect and the above examples, the repeat region includes at least 4 repeat units. For example, the repeat region includes at least 6 repeat units, such as at least 10 repeat units. In a particular example, the repeat region includes 10 to 30 repeat units.

In an additional example of the first aspect and the above examples, the segment further includes a common region and a variant region and wherein the set of probes includes a second probe complementary to the common region and a third probe complementary to the variant region. For example, the segment further includes a second common region, the set of probes further including a fourth probe complementary to the second common region. In a further example, the variant region corresponds to a deletion variation. In another example, the variant region corresponds to a disease variation.

In a further example of the first aspect and the above examples, the set of probes is formed of different nucleic acids than the segment. For example, the different nucleic acids include LNA, PNA, or a combination thereof.

In another example of the first aspect and the above examples, the first probe includes an appended chemical group. For example, the appended chemical group is larger than a pore opening of the nanopore device. In another example, the appended chemical group is reactive with the nanopore device.

In an additional example of the first aspect and the above examples, measuring the signal includes measuring current spikes corresponding to stripping the probes. For example, the method further includes correlating characteristics of the current spikes to determine genotype.

In a further example of the first aspect and the above examples, the method further includes repeating, directing, stripping, and measuring.

In another example of the first aspect and the above examples, the set of probes includes second and third probes complementary to regions of the segment of single stranded nucleic acids different than the repeat region.

In a second aspect, a method of determining genotype includes receiving a current trace including current spikes associated with translation of a strand of nucleic acids through a nanopore and stripping probes from the strand, the probes associated with a repeat unit of the strand of nucleic acids. The method further includes determining a genotype based on a characteristic of the current spikes.

In an example of the second aspect, the characteristic includes a number of the current spikes.

In another example of the second aspect and the above examples, the characteristic includes a period between consecutive current spikes.

In an additional example of the second aspect and the above examples, determining the genotype includes correlating a number of the current spikes with the genotype.

In a third aspect, a method of determining genotype includes mixing a set of binding probes with a set of single stranded nucleic acid segments. The set of single stranded nucleic acid segments includes a first segment associated with a first gene and a second segment associated with a second gene. The first segment includes a first repeating section of first repeating units. The second segment includes a second repeating section of second repeating units. The set of binding probes includes a first probe complementary to the first repeating units, a second probe uniquely associated with the first segment and complementary to a region of the first segment, and a third probe complementary to the second repeating units. The method further includes directing the segments through a nanopore device, stripping the probes of the set of probes from the segments, and measuring a current through the nanopore device to provide a current trace. The current trace includes current spikes indicative of stripping the first probe and the second probe.

In an example of the third aspect, the method further includes a fourth probe uniquely associated with and complementary to a region of the second segment.

In another example of the third aspect, the method further includes a fourth probe uniquely associated with and complementary to a region of the first segment.

In a fourth aspect, a kit includes a probe having a sequence complementary to a repeat unit of a repeat region of a segment of single stranded nucleic acids associated with an allele.

In an example of the third aspect, the method further includes a second probe having a sequence complementary to a mutation of the repeat unit.

In a fifth aspect, a kit includes a first probe having a sequence complementary to a common region of a segment of single stranded nucleic acids associated with a gene and a second probe having a sequence complementary to a variant region of the segment of single stranded nucleic acids associated with the gene.

In an example of the fifth aspect, the method further includes a third probe having a sequence complementary to a second common region of the segment of single stranded nucleic acids associated with the gene.

In a sixth aspect, a method of determining genotype includes receiving a current trace including current spikes associated with translation of a strand of nucleic acids through a nanopore. The strand includes double stranded regions associated with hybridized probes. The probes are associated with a tandem repeat segment of the strand of nucleic acids. The method further includes determining a genotype based on a characteristic of the current spikes.

In an example of the sixth aspect, the characteristic includes a number of the current spikes. In another example, the characteristic can include a period between consecutive current spikes. In an additional example, the characteristic can include a period between first and last spikes.

In a further example of the sixth aspect and the above examples, determining the genotype includes correlating a number of the current spikes with the genotype.

In an additional example of the sixth aspect and the above examples, determining the genotype includes correlating a period between current spikes with the genotype.

Note that not all of the activities described above in the general description or the examples are required, that a portion of a specific activity may not be required, and that one or more further activities may be performed in addition to those described. Still further, the orders in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of detecting an allele of a human identification panel, the method comprising:

binding specifically a set of probes to a single stranded nucleic acid segment derived from a locus of the human identification panel, the segment including a microsatellite region having between 5 and 30 k-mer repeat units, wherein k is in a range of 2 to 6, the set of probes including a first subset of k-mer binding probes complementary to the k-mer repeat units;

directing the segment through a porin protein nanopore of a nanopore device with an applied voltage, the bound set of probes being stripped from the segment as the segment passes through the porin protein nanopore;

measuring with the nanopore device an ion current signal including current spikes corresponding to the stripping of probes of the first subset of k-mer binding probes as the segment passes through the protein nanopore of the nanopore device, a number of current spikes of the ion current signal indicative of the number of k-mer repeat units;

detecting the allele based on a characteristic of the current spikes of the ion current signal, wherein the characteristic includes the number of the current spikes.

2. The method of claim 1, wherein the set of probes includes a second subset of k-mer binding probes complementary to a mutation of the k-mer repeat units.

3. The method of claim 1, wherein the first subset of k-mer binding probes complementary to the k-mer repeat units is complementary to at least two consecutive k-mer repeat units.

4. The method of claim 1, wherein the first subset of k-mer binding probes complementary to the k-mer repeat units is complementary to a subset of consecutive nucleotides in at least two adjacent k-mer repeat units.

5. The method of claim 1, wherein the segment further includes a common region and a variant region and wherein the set of probes includes a second probe complementary to the common region and a third probe complementary to the variant region.

6. The method of claim 5, wherein the segment further includes a second common region, the set of probes further including a fourth probe complementary to the second common region.

7. The method of claim 1, wherein the first subset of k-mer binding probes includes an appended chemical group.

8. The method of claim 7, wherein the appended chemical group is larger than a pore opening of the nanopore device.

9. The method of claim 7, wherein the appended chemical group is reactive with the nanopore device.

10. The method of claim 1, wherein the set of probes includes second and third probes complementary to regions of the single stranded nucleic acid segment different than the microsatellite region.

* * * * *

SEQUENCE LISTING

```
<160> NUMBER OF SEQ ID NOS: 6

<210> SEQ ID NO 1
<211> LENGTH: 12
<212> TYPE: DNA
<213> ORGANISM: Homo sapiens

<400> SEQUENCE: 1
gatgatgatg at                                                          12

<210> SEQ ID NO 2
<211> LENGTH: 15
<212> TYPE: DNA
<213> ORGANISM: Homo sapiens

<400> SEQUENCE: 2
gaagaagaag aagaa                                                       15

<210> SEQ ID NO 3
<211> LENGTH: 15
<212> TYPE: DNA
<213> ORGANISM: Homo sapiens

<400> SEQUENCE: 3
gaagaagatg aagaa                                                       15

<210> SEQ ID NO 4
<211> LENGTH: 12
<212> TYPE: DNA
<213> ORGANISM: Homo sapiens

<400> SEQUENCE: 4
gaagaagatg aa                                                          12

<210> SEQ ID NO 5
<211> LENGTH: 146
<212> TYPE: DNA
<213> ORGANISM: Homo sapiens
```

```
<400> SEQUENCE: 5
tcccaagctc ttcctcttcc ctagatcaat acagacagaa gacaggtgga tagatagata      60
gatagataga tagatagata gatagataga tatcattgaa agacaaaaca gagatggatg     120
atagatacat gcttacagat gcacac                                          146

<210> SEQ ID NO 6
<211> LENGTH: 88
<212> TYPE: DNA
<213> ORGANISM: Homo sapiens

<400> SEQUENCE: 6
tattccattg tatctatctg tctgtctgtc tatctatcta tctatctatc tatctatcta     60
tctatctatc tatctatcac agtttctt                                        88
```